US006811971B2

(12) United States Patent
Klepp et al.

(10) Patent No.: US 6,811,971 B2
(45) Date of Patent: Nov. 2, 2004

(54) METHOD FOR THE DETECTION OF INFLUENZA A/B VIRUSES

(75) Inventors: Juergen Klepp, Graben-Neudorf (DE); Reiner Schlipfenbacher, Bad Duerkheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 10/311,523

(22) PCT Filed: Jun. 15, 2001

(86) PCT No.: PCT/EP01/06735

§ 371 (c)(1),
(2), (4) Date: Dec. 13, 2002

(87) PCT Pub. No.: WO01/96595

PCT Pub. Date: Dec. 20, 2001

(65) Prior Publication Data

US 2003/0143530 A1 Jul. 31, 2003

(30) Foreign Application Priority Data

Jun. 15, 2000 (DE) .......................................... 100 28 837

(51) Int. Cl.⁷ ............................ C12Q 1/70; C12Q 1/06; G01N 33/53; C12N 1/00
(52) U.S. Cl. ............................ 435/5; 435/7.1; 435/39; 435/810
(58) Field of Search ............................... 435/5, 7.1, 39, 435/810

(56) References Cited

U.S. PATENT DOCUMENTS 5,714,341 A  2/1998  Thieme et al. ................. 435/22
6,015,664 A  1/2000  Henrickson et al. ............ 435/5

FOREIGN PATENT DOCUMENTS

| EP | 1010981 A1 | 6/2000 | ......... G01N/33/569 |
| FR | 2708348 A1 | 2/1995 | ......... G01N/33/546 |
| WO | WO 92/12256 | 7/1992 | ............ C12Q/1/00 |

OTHER PUBLICATIONS

Atmar, Robert L. et al., "Comparison of Reverse Transcription–PCR with Tissue Culture and Other Rapid Diagnostic Assays for Detection of Type A Influenza Virus," Journal of Clinical Microbiology, Oct. 1996, p. 2604–2606.
Covalciuc, Kristi A. et al., "Comparison of Four Clinical Specimen Types for Detection of Influenza A and B Viruses by Optical Immunoassay (FLU OIA Test) and Cell Culture Methods," Journal of Clinical Mircobiology, Dec. 1999, p. 3971–3974.
Donofrio, James C. et al., "Detection of Influenza A and B in Respiratory Secretions with the Polymerase Chain Reaction," PCR Methods and Applications, pp. 263–268 (1992).
Willers, Hildegard, "Influenza Virus," Microbiological Diagnostics, 1992, 15 pages.

Primary Examiner—Hankyel T. Park

(57) ABSTRACT

The invention concerns a method for the detection of an infection with influenza A and/or influenza B virus comprising the steps: i) obtaining a saliva sample, ii) preparing the saliva sample for a detection reaction and iii) detecting the influenza A and/or influenza B virus in the saliva sample. The invention in addition concerns a test kit for the detection of an infection by the influenza A and/or influenza B virus containing: i) a device for the collection of a saliva sample and ii) reagents and auxiliary agents for the detection of influenza A and/or influenza B viruses. Furthermore the invention concerns the use of saliva as a sample material for the detection of an infection with the influenza A and/or influenza B virus.

18 Claims, No Drawings

METHOD FOR THE DETECTION OF INFLUENZA A/B VIRUSES

FIELD OF THE INVENTION

The invention concerns a method for the detection of influenza A/B viruses, a corresponding test kit and the use of saliva as a sample material for the detection of influenza A/B viruses.

BACKGROUND OF THE INVENTION

Influenza is a frequently underestimated infectious disease which can result in high morbidity and mortality rates especially in elderly persons and in high-risk patients. Influenza A and/or influenza B viruses (also abbreviated influenza A/B viruses in the following) are responsible for genuine virus influenza which is contracted by several 100 million persons worldwide each year. The influenza A and B viruses primarily infect the nasopharyngeal and oropharyngeal cavities and initially cause general respiratory symptoms in the affected persons.

It is not possible even for experienced medical professionals to very reliably diagnose influenza solely on the basis of the patient's clinical symptoms since other viruses which infect the nasal or pharyngeal cavity such as adenoviruses, parainfluenza viruses or respiratory syncitial viruses (RS viruses) cause similar symptoms.

Due to the high medical importance of influenza infections (flu), almost every country in the world now has a nationally organized influenza monitoring system. For this scheme general practioners remove swabs from the nose and/or throat and send them to the respective national reference centre. The influenza A/B viruses are then usually detected by eluting the swabs and subsequently culturing the patient specimens on mammalian cells such as MDCK cells (Madine-Darby Canine Kidney cells).

The culture in these special laboratories can take up to 14 days and is thus not of immediate relevance for the diagnosis of the individual patients. Rather the goal of the national reference centres is to type and subtype the cultured viruses and to report the results to the World Health Organisation (WHO). The job of the vaccine manufacturer is then to adapt next year's influenza vaccines to the latest circulating viral strains on the basis of the annual WHO recommendation.

The reason for the high degree of genetic and hence immunological variability especially of the influenza A viruses is due to the fact that a genetic shift (reassortment of the viral genes) can also occur in rare cases in addition to the usual genetic drift (point mutation). This is due to the fact that, in contrast to other viruses, the genome of the influenza viruses is segmented and that influenza A is a pathogen in humans as well as in animals.

The immunodominant antigens present on the surface of the virus are haemagglutin (H) and neuraminidase (N). At present 15 subtypes of haemagglutin (H1–H15) and 9 subtypes of neuraminidase (N1–N9) are known for influenza A.

If for example a host (e.g. a pig) is coinfected with an influenza virus of the A type which is pathogenic for man and with an influenza A bird virus this can result in a reassortment of the viral genome to form a new influenza A virus subtype which then completely evades the human immune system when it is transferred back to humans. The most recent example of this was the occurrence of the so-called avian virus influenza in May 1997 in Hong Kong (type A/H5N1/Hong Kong/156/97) in which 6 of the 18 affected patients died despite an early detection and intensive medical care.

However, in order to cause a larger epidemic or even a worldwide pandemic, a new influenza virus subtype must be transmitted directly from human to human as was the case in 1918/1919 for the first occurrence of the subtype H1N1 (Spanish flu, worldwide ca. 50 million deaths), 1957 (H2N2, Asian flu, ca. 1 million victims) and 1968 (H3N2 Hong Kong flu, ca. 1 million victims).

A new generation of influenza agents has recently become available, the so-called neuraminidase inhibitors which for the first time allow a causal treatment of influenza and are thus regarded among experts as a true breakthrough in the treatment of influenza. Clinical studies carried out for the registration of this new class of substance showed that successful treatment primarily depends on an early start to treatment after the first clinical symptoms occur. Hence in view of this new therapeutic option, the necessity to begin the treatment at an early stage and the relatively unspecific clinical symptoms, a rapid individual diagnosis would be helpful as a basis for treatment decisions.

As a result several diagnostic manufacturers have recently developed rapid immunological influenza tests based on antigen detection and these rapid tests are nasal and/or throat swabs or liquid obtained by nasal irrigation as the sample material. Examples of such rapid influenza tests are the Influenza A/B Rapid Test from Roche Diagnostics GmbH, Quick Vue® from Quidel and AB FLU OLA® from Biostar.

A particular problem in collecting samples is to remove sample material from the affected region of the nasal and pharyngeal cavity which contains sufficient amounts of influenza A and/or influenza B viruses (abbreviated to influenza A/B viruses in the following). Hence the quality of sampling has a direct influence on the positivity rate of the rapid tests which usually have a clinical sensitivity of about 70% i.e. the immunological rapid test is also positive in 70% of all samples that are assessed to be influenza positive by the reference method (cell culture). Hence the diagnostic manufacturers point out in the package inserts for their influenza rapid tests that the specimens should only be collected by specially trained medical personnel in order to ensure that the specimen material obtained does in fact contain adequate amounts of influenza A/B viruses.

The situation is further complicated by the fact that the regions in the pharyngeal cavity that have to be swabbed (posterior pharyngeal wall, pharynx, tonsils) can indeed differ depending on the viral infection that is present. This for example means that a swab has to be taken of other regions of the throat in order to detect a streptococcal infection than for example to detect influenza A/B viruses.

Taking a nose/throat swab is unpleasant for patients and a particular problem in the case of (small) children. On the other hand children are the main carriers of virus influenza at least in the early phase of an influenza epidemic due to their social contacts (kindergarten, school) and the fact that their immune system is often not yet fully developed.

Since nose and throat swabs are not a homogeneous sample material, the positivity rate of an influenza test is, in addition to the quality of the swab, also determined by the correct elution i.e. the transfer of the swab material to a liquid phase which then serves as the actual sample material in the subsequent test.

Especially the new therapeutic option (neuraminidase inhibitors) will in future result in an increasing need for flu virus tests (influenza A/B viruses) for general practitioners or the patients which is not compatible with the previously used sample material (swab, nasal irrigation) that requires that specimens be taken by trained (medical) personnel.

The object of the present invention is to eliminate the disadvantages of the prior art. In particular the object of the invention is to provide a method for detecting an influenza A and/or influenza B virus infection which can be carried out by untrained personnel or ideally by the patients themselves. Above all it is an object of the invention to find a sample material from which influenza A and/or influenza B viruses can be reliably detected which is preferably homogeneous and can be collected by untrained personnel or ideally by the patient themselves in a simple and uncomplicated manner.

SUMMARY OF THE INVENTION

The invention concerns a method for the detection of an infection with the influenza A and/or influenza B virus comprising the steps i) obtaining a saliva sample from the individual to be examined ii) preparing the saliva sample for the detection or a detection reaction and iii) detecting the influenza A and/or influenza B virus in the saliva sample.

The invention additionally concerns a test kit for detecting an infection with the influenza A and/or influenza B virus containing i) a device for collecting a saliva sample and ii) reagents and auxiliary agents for the detection of influenza A and/or influenza B viruses.

Finally the invention concerns the use of saliva as a sample material to detect an infection with the influenza A and/or influenza B virus.

DETAILED DESCRIPTION

It was surprisingly found that it is possible to reliably detect influenza A/B viruses from saliva as a sample material using established diagnostic methods.

In particular it is surprising that in a preferred embodiment of the invention it is possible to detect influenza A/B viruses from saliva without having to enrich the viruses in the saliva sample when taking a sample, but rather spontaneously formed saliva is adequate as a sample material for detecting influenza A/B viruses. Spontaneously formed saliva is understood in the present invention to mean that in order to detect influenza A/B viruses, the influenza A/B viruses are not enriched in the sample when the saliva sample is collected. Only the saliva that is present spontaneously in the mouth cavity is collected and for example transferred to a saliva collecting vessel (e.g. by spitting etc.). It is also possible to collect the saliva sample in the mouth cavity with the aid of an absorbent material such as a cotton fleece (swab) or to use saliva collecting devices familiar to a person skilled in the art (such as the so-called SALIVETTES® from Sarstedt, Newton, N.C., or the ORA-SURE® specimen collection device from Epitope Inc. Beaverton, Oreg.) to collect the saliva sample.

Of course it is also possible according to the invention to use saliva as a sample material for the detection of influenza A/B viruses in which an enrichment (concentration) of the viruses has occurred during the sampling or in subsequent processing steps.

In contrast to the previously known sample materials in influenza diagnostics i.e. nose/throat swabs and liquid obtained by nasal irrigation, the saliva sample material according to the invention and the simple manner of sample collection allows, a standardized sample collection by untrained persons or by the patients themselves and thus increases the diagnostic reliability of influenza A/B virus tests. Moreover saliva is a more homogeneous sample material than the other previously used materials which also contributes to the diagnostic reliability.

In the method according to the invention a saliva sample is firstly collected. This can for example be carried out as already described above by spitting into a vessel, absorbing a saliva sample by means of an absorbent material such as a cotton swab or similar materials in the oral cavity or by using a conventional saliva collecting device.

The saliva sample is subsequently prepared for the detection reaction in accordance with the detection method to be used (immunological detection or detection by means of nucleic acids).

For the immunological detection the viral nucleoprotein of influenza A/B viruses is for example released from the saliva sample by lysing reagents. Such reagents are known to a person skilled in the art and can for example contain salts or detergents as the active components for the lysis. Lysing reagents for the detection of influenza viruses preferably contain a detergent (for example TRITON®X100, TWEEN®20 or beta-octylglycopyranoside have proven to be suitable), a mild reducing agent (for example N-acetyl L-cysteine or DTT=dithiothreitol), physiological saline (i.e. 0.9% by weight NaCl in 20–50 mM phosphate buffer), a preservative (for example 0.09% by weight $NaN_3$) and optionally a protein to reduce unspecific binding (for example BSA=bovine serum albumin or BPLA=bovine plasma albumin). In addition to the viral nucleoprotein, the immunological test can for example also detect the viral matrix protein or the viral polymerases. It is also possible to detect the haemagglutinin or the neuraminidase of the influenza A/B viruses in which case no lysis is required since these viral components are present on the viral surface.

If the detection is based on a nucleic acid, a viral nucleic acid (RNA) is for example isolated, purified and appropriately amplified in the presence of the primers required for the detection, preferably by means of the reverse transcriptase polymerase chain reaction (RT-PCR). These steps are known to a person skilled in the art as are nucleic acid tests without prior amplification.

The influenza A/B viruses are detected in the saliva sample by known methods.

In the case of an immunological detection of for example the viral nucleoprotein, a sandwich complex can be formed using appropriately labelled antibodies and detected. Competitive test formats are of course also possible. Although the detection is preferably by means of an immunochromatographic test strip that can be visually evaluated as a rapid test, the detection can be carried out by means of all conventional immunological methods, for example ELISA, agglutination tests, turbidimetric tests etc.

If the influenza A/B viruses are detected by means of nucleic acids such as RNA, the product of the RT-PCR is preferably labelled by means of a labelled primer and the label on the primer (e.g. an enzyme or fluorescent label) is detected according to the type of label.

A test kit for carrying out the method according to the invention is also a subject matter of the invention. The test kit contains as an important component firstly a device for collecting a saliva sample such as a vessel for spitting into, one or more absorbent cotton swabs or a conventional saliva collection device e.g. a SALIVETTE® device from the Sarstedt, Inc, or an ORASURE® specimen collection device from the Epitope Inc. In addition the test kit contains all reagents and auxiliary reagents required to detect the influenza A/B viruses in the saliva sample. In the case of an immunological detection, these are for example a lysing buffer to release the viral nucleoproteins, optionally labelled antibodies and optionally a reaction medium (test strips, microtitre plate, test tubes) for carrying out the immunological detection. The corresponding reagents and auxiliary agents are known to a person skilled in the art in numerous embodiments. The same applies to the nucleic acid test. In this case the kit for example contains the required PCR reagents and reaction vessels.

The invention is further elucidated by the following example:

EXAMPLE

1. Detection of an Influenza Virus Infection from Saliva as the Sample Material In order to demonstrate the suitability of saliva as a sample material for detecting influenza viruses, two throat swabs and one saliva sample were taken from 10 persons suspected to have an influenza infection and 4 persons which were not suspected of having influenza. The sample material obtained from the throat swabs was collected for comparative purposes and examined for an influenza A/B virus infection. The results of these investigations were compared with the results obtained using saliva as the sample material. Table 1 which is shown at the end of the experimental part of the example shows an overview of the comparative results.

1.1 Sample Collection
1.1.1. Throat Swabs

The throat swabs were taken using sterile disposable cotton swabs from the Copan Italia S.p.a. (Brescia, Italy; order No. 167CS01) in the manner familiar to a person skilled in the art. The two throat swabs taken from each patient were obtained by swabbing the throat once with a swab having two cotton pads located directly adjacent to one another. This ensures that the two swabs are substantially comparable.

1.1.2. Saliva Sample

The saliva sample was collected by the patients themselves by collecting ca. 0.5 ml spontaneously formed saliva in a small disposable plastic tube with a screw cap (order No. 62.559.001 from the Sarstedt Inc.). The saliva collecting methods and devices known to a person skilled in the art (such as SALIVETTES® from the Sarstedt Inc. of the ORASURE® specimen collection device from Epitope Inc.) were intentionally not used in order to demonstrate that it is possible to detect influenza viruses without prior concentration or saliva processing. Of course it is equally possible according to the invention to use such saliva collecting methods and devices.

1.2 Detection of Influenza A/B Viruses from Throat Swabs (Only for Comparison)
1.2.1 Detection from Throat Swabs by Means of Cell Culture The first throat swab in each case was immediately transferred after collection to a tube containing 1.5 ml influenza virus transport medium from Virotest GmbH (Stuttgart, Germany, Cat. No. 0500300) and cultured on MDCK cells (Madine-Darby Canine Kidney cells). The samples were cultured according to the methods described in the literature ("Mikrobiologische Diagnostik", Georg Thicme editor, Stuttgart, New York, 1992, publisher Friedrich Burkhard, page 371). The results are shown in table 1 in which "+" represents a positive result and "−" represents a negative result.

1.2.2 Detection from the Throat Swab by Means of an Immunological Rapid Test

The second swab was in each case examined immediately after removing the sample from the throat of the patient by means of an immunological antigen rapid test for the presence of influenza viruses (Influenza A/B Rapid Test from Roche Diagnostics GmbH, Mannheim, Germany, cat. No. 2 158 663). The rapid test used in this case corresponds essentially to the immunological rapid test described as example 2 in EP-A 0 926 498. Reference is herewith expressly made to this document.

In addition to the visual evaluation of the test strips, the intensity of the detection line after completion of the chromatography was quantitatively measured by means of a remission photometric instrument (ring illumination using 24 green LEDs at a wavelength of 555 nm and CCD camera with a lens). The intensity of the detection line signal was examined as a percentage of the remission (% rem; relative to a "white" area of the test strip which was assigned a remission of 100%): remission values above 98.5% are detected as a negative signal by the user; remission values between 96% and 98.5% are detected as a weakly positive signal; remission values of less than 96% are detected as an unequivocally positive signal. The results are shown in table 1 in which "+" denotes a positive signal, "(+)" denotes a weakly positive signal and "−" denotes a negative signal.

1.3 Detection of Influenza A/B Viruses from Saliva
1.3.1. Detection of Viral Nucleic Acid in the Saliva by Means of RT-PCR The saliva samples were examined by means of RT-PCR (reversed transcriptase polymerase chain reaction) for the presence of viral influenza nucleic acid (in this case ribonucleic acid, RNA). The analytical process comprises the three conventional partial steps in nucleic acid diagnostics of sample preparation (in order to separate inhibitors), amplification and detection of the nucleic acid (cf. 1.3.1.a to 1.3.1.c in the following). The procedure was as follows:

1.3.1.a Sample Preparation

The commercially available High Pure Viral RNA Kit from Roche Molecular Bio-chemicals (Mannheim, Germany; order No. 1 858 882) was used to isolate the viral influenza RNA. The procedure was according to the standard protocol described in the product description by firstly binding 200 µl saliva per reaction vessel (filter tube) to the glass fleece of the filter tube in the presence of binding buffer and, after removing inhibitors that may be present by two wash steps, eluting the viral nucleic acid in 200 µl elution buffer. In this process care was taken that the sample volume before (saliva) and after (eluate) the sample preparation was identical so that no concentration of the influenza viruses had taken place. Of course, it is also possible according to the invention to carry out the elution step with a smaller amount of elution buffer than the quantity of saliva and thus to concentrate or enrich the influenza viruses in the eluate.

1.3.1.b RT-PCR

If not listed otherwise all reagents were obtained from Roche Molecular Biochemicals (see above).

The reaction volume per PCR reaction vessel was 50 µl. This contained 10 µl sample volume (eluate from the sample preparation) and 10 µl bicine buffer (5×RT-PCR buffer). The other components of the master mix were present in the following final concentration: 2.5 mmol/l manganese acetate, 0.2 mmol/l of each of the following dATP (2'-deoxyadenosine-5' triphosphate), dCTP (2'deoxycytidine-5' triphosphate), dGTP (2'-deoxyguanosine-5' triphosphate)

and dUTP (2'-deoxyuridine-5 tri-phosphate) and 0.05 mmol/l dTTP (2'-deoxythymidine-5' triphosphate); 0.01 U/µl UNG (uracil DNA glycosylase); 0.2 U/µl Tth polymerase from *Thermus thermophilus* HB8; 0.8 U/µl RNase inhibitor and 1.0 µmol/l of forward and reverse primer.

The sequence of the primers was obtained from the literature (James C. Donofrio et al., Detection of Influenza A and B in Respiratory Secretions with the PCR, 1992, PCR Methods and Applications 1, page 263–268). The primers are type-specific for influenza A and have a highly conserved gene segment (position 101 to 312) of the matrix gene of 212 base pairs in length. The reverse primer was labelled at the 5' end with biotin for subsequent detection of the amplification product in the microtitre plate. Type-specific primers for influenza B are also known in the literature (James C. Donofrio et al., Detection of Influenza A and B in Respiratory Secretions with the PCR, 1992, PCR Methods and Applications 1, page 263–268).

The master mix was amplified in a Perkin Elmer 9600 thermocycler using the following temperature profile: 20 minutes room temperature after addition of UNG+45 minutes 60° C.+2 minutes 94° C.+10 cycles (30 seconds 94° C.+60 seconds 50° C.+90 seconds 68° C.)+35 cycles (30 seconds 94° C.+60 seconds 60° C.+90 seconds 68° C.)+7 minutes 68° C.

1.3.1c Hybridization and Detection

The nucleic acid amplified by the RT-PCR was detected using the PCR ELISA (DIG detection) from Roche Molecular Biochemicals cat. No. 1 636 111. With the exception of the pipetting volumes, all steps were carried out according to the package insert.

10 µl of the amplification product was mixed with 20 µl denaturating solution in a 1.5 ml reaction vessel and incubated for 10 minutes at room temperature. Afterwards 250 µl of a digoxigenin-labelled hybridization probe was added. The concentration of the hybridization probe was 70 ng/ml.

The sequence of the hybridization probe was obtained from the literature (James C. Donofrio et al., Detection of Influenza A and B in Respiratory Secretions with the PCR, 1992, PCR Methods and Applications 1, page 263–268). The probe is directed against position 177–205 of the matrix gene (segment 7) of influenza A. Corresponding probes for influenza B are also known from the literature (James C. Donofrio et al., Detection of Influenza A and B in Respiratory Secretions with the PCR, 1992, PCR Methods and Applications 1, page 263–268).

200 µl of the reaction mixture was transferred to a well of a streptavidin-coated microtitre plate and incubated on a shaker for 1 hour at 37° C. After binding the hybridization product to the streptavidin of the microtitre plate wall, the contents of the wells were aspirated and washed three times with 300 µl wash solution each time. Afterwards 200 µl anti-digoxigenin-peroxidase substrate (anti-DIG-POD conjugate) was added to the well and the solution was incubated for 30 minutes at 37° C. on a shaker. After binding the POD conjugate the contents of the wells were aspirated, washed 3 times with 300 µl wash solution and subsequently 200 µl 2,2'-azino-di-[3-ethylbenzthiazoline sulfonate (6)] diammonium salt substrate (ABTS substrate) was added. After a final incubation for 30 minutes at 37° C., the colour development at 405 nm was measured on a microtitre plate reader.

For each PCR determination of saliva samples, several negative controls (DEMC water) (article No. 16-001Y, ACCUGENE® Water, molecular biology grade, autoclaved, manufactured by Cambrex Bio Science Verviers S.P.R.L., Verviers, Belgium) were carried out in parallel to exclude false-positive values by contamination and several positive controls (dilution series of MDCK culture supernatant containing influenza viruses) were determined in parallel by sample preparation and RT-PCR. In addition an internal kit positive control was also carried out in order to check the detection reagents on the microtitre plate.

The absorbance values of the parallel negative controls in the microtitre plate were usually 100–150 mA. The values of the internal positive control of the kit that was carried out in parallel were usually 1000–1500 mA.

Absorbance values of =300 mA were defined as a positive signal for patient samples which corresponds to a signal that was more than twice the blank or zero value. The results are shown in table 1 in which "+" denotes a positive result and "−" denotes a negative result.

1.3.2. Detection of a Viral Antigen in Saliva by Means of an Immunological Rapid Test The Influenza A/B Rapid Test from Roche Diagnostics GmbH (cat. No. 2 158 663) was used to detect influenza A/B viruses in saliva. The rapid test that was used corresponds essentially to the immunological rapid test described as example 2 in EP-A 0 926 498. Reference is expressly made herewith to this document.

The test is usually used to type-specifically detect viral nucleoprotein in throat swabs by means of an immunological chromatographic test strip. The test does not differentiate between influenza A and influenza B viruses.

In order to ensure a good chromatography of the test strip using saliva as the sample material, a special lysing/elution buffer was used which is not a component of the test kit. The special lysing/elution buffer has the following composition:

0.9% by weight NaCl, 2 mM $KH_2PO_4$, 10 mM $Na_2HPO_4$, 0.095% by weight $NaN_3$, 10 mM EDTA, 1.5% by weight bovine serum albumin (BSA), 1.5% by weight Triton®X-100.

The test was carried out as follows:

Instead of firstly eluting a throat swab as the patient sample with 3 portions (=800 µl) of the lysing/elution buffer contained in the test kit as described in the package insert, 300 µl saliva and 500 µl of the special lysing/elution buffer were added to a reaction vessel and mixed.

The remaining test procedure was carried out according to the steps described in the package insert. This comprises firstly adding two drops of antibody solution 1 (contains biotinylated monoclonal antibodies against nucleoprotein A and nucleoprotein B), adding two drops of antibody solution 2 (contains digoxigenylated monoclonal antibodies against nucleoprotein A and nucleoprotein B) and subsequently chromatographing this reaction mixture on a test strip.

As known from EP-A 0 926 498 the test strip contains a conjugate fleece which is reversibly impregnated with a gold conjugate that can be detached in the sample liquid. The gold particles are adsorptively coated with a monoclonal antibody against digoxigenin.

A nitrocellulose membrane on which polystreptavidin as a detection line and a polyclonal antibody PAB<mouse Fcγ>S-IgG as a control line are irreversibly impregnated is located in another zone of the test strip downstream in the direction of chromatography.

The sandwich complex formed in the reaction vessel in the presence of the analyte comprising biotinylated antibody/nuleoprotein/digoxigenylated antibody chromatographs across the test strip, binds the gold conjugate after it has been solubilized via the anti-digoxigenin antibody to the digoxigenin-labelled anti-influenza antibody of the sandwich complex and is subsequently captured on the polystreptavidin line on the nitrocellulose membrane by means of the biotin-labelled anti-influenza antibody of the sandwich complex. As a result a red line becomes visible on the nitrocellulose membrane which represents a positive test signal.

Excess gold conjugate chromatrographs downstream and is captured on the control line of the nitrocellulose membrane as another visible red line by means of PAB<mouse Fcγ>S-IgG.

In addition to the visual evaluation of the test strips, the intensity of the detection line after completion of the chromatography was quantitatively measured by means of a remission photometric instrument (ring illumination using 24 green LEDs at a wavelength of 555 nm and CCD camera with a lens). The intensity of the detection line signal was examined as a percentage of the remission (% rem; relative to a "white" area of the test strip which was assigned a remission of 100%); remission values above 98.5% are detected as a negative signal by the user; remission values between 96% and 98.5% are detected as a weakly positive signal; remission values of less than 96% are detected as an unequivocally positive signal. The results are shown in table 1 in which "+" denotes a positive signal, "(+)" denotes a weakly positive signal and "−" denotes a negative signal.

1.4. Results

Some results obtained with patient samples are shown in the following as an example (Table 1).

These results relate exclusively to the detection of influenza A viruses since only influenza A was predominant at the time of sample collection and no patient samples with influenza B were found. Experts know that influenza B, in contrast to influenza A, does not circulate in every winter season and even if both influenza A/B viruses occur in a winter season, influenza B is always much less prevalent.

It should also be mentioned that artificially prepared influenza B-positive saliva samples (pooled saliva samples which have been spiked with a culture supernatant of influenza B viruses) were also suitable for detecting influenza viruses in saliva in the nucleic acid test as well as in the immunological test. The results shown do not therefore represent a limitation in the sense of the invention with regard to separate or joint detection of influenza B viruses in addition to influenza A viruses from saliva. Rather saliva is suitable as a sample material for the detection of influenza A/B viruses.

TABLE 1

| Person No.[A] | Throat swab samples (only for comparison) | | | | Saliva samples | |
|---|---|---|---|---|---|---|
| | | immunological rapid test | | PCR | immunological rapid test | |
| | culture[B] | visual[C] | photometric[D] | result[E] | visual[C] | photometric[D] |
| 1 | + | + | + | + | + | + |
| 2 | + | (+) | (+) | + | + | + |
| 3 | + | (+) | (+) | + | + | + |
| 4 | + | + | + | + | + | + |
| 5 | + | + | + | + | + | + |
| 6 | + | (+) | (+) | + | + | + |
| 7 | + | − | − | + | (+) | (+) |
| 8 | + | − | − | + | (+) | (+) |
| 9 | − | − | − | − | − | − |
| 10 | − | − | − | − | − | − |
| 11 | − | − | − | − | − | − |
| 12 | − | − | − | − | − | − |
| 13 | − | − | − | − | − | − |
| 14 | − | − | − | − | − | − |

[A]Persons No. 1–10 were persons with influenza-like symptoms. Persons No. 11–14 were persons without acute respiratory symptoms.
[B]Culture on MDCK cells (cf. 1.2.1 above); + positive; − negative
[C]Rapid test procedure as described under 1.2.2. and 1.3.2. (see above); + positive; (+) weakly positive; − negative
[D]Quantitative determination of the intensity of the detection line by means of a remission-photometric measuring instrument (cf. under 1.2.2. and 1.3.2. above); only the relative results are shown (+ positive; (+) weakly positive; − negative) which are according to the scale given in the text.
[E]The absorbance values of the microtitre plate were measured at 405 nm (cf. under 1.3.1. above); only the relative results are shown (+ positive; − negative) which are according to the scale given in the text.

The following is apparent from the results shown in Table 1:

Not all persons (No. 1–10) classified as influenza patients according to the clinical symptoms were in fact influenza positive. Persons No. 9 and 10 were negative in the culture of the throat swab as well as in the PCR of the saliva as well as in the rapid test of the saliva and throat swab. This emphasizes the statement made in the introduction and known among experts that it is not possible to make a definitive diagnosis for influenza solely on the basis of clinical symptoms.

The throat swabs and saliva samples of asymptomatic persons (No. 11–14) were negative with all listed test methods which demonstrates the clinical specificity of these methods.

Of the eight persons found to be influenza A positive by means of cell culture by throat swabs (No. 1–8; so-called culture-positive persons), six persons were also diagnosed as positive with the immunological rapid test using throat swabs. This illustrates that the clinical sensitivity of these previously available rapid tests using swabs as a sample material is less than that of the cell culture which is recognized at present as the gold standard (clinical sensitivities of various immunological rapid tests according to the package inserts of the respective manufacturers: Quidel 73% for nose swabs, Roche 70% for throat swabs, Biostar 60% for throat swabs and 83% for nasopharyngeal swabs).

In contrast the corresponding saliva samples from all eight culture-positive patients were found to be positive with the immunological rapid test.

Furthermore the comparison of the remission values (not shown in the table) shows that the intensities of the detection line on the immunological rapid test strips using saliva samples were somewhat more intensive than the corresponding intensities of the detection line when using throat swabs.

The results of the rapid tests of saliva are thus in agreement with the corresponding PCR results from saliva and demonstrate that influenza A/B viruses can be reliably detected in saliva as a sample material even without prior enrichment during the sample collection.

What is claimed is:

1. A method for determining whether a subject is infected with an influenza A virus and/or an influenza B virus comprising detecting at least one of influenza A virus or influenza B virus in a saliva sample from the subject.

2. The method of claim 1, wherein the saliva sample is obtained from spontaneously formed saliva.

3. The method of claim 1, wherein the saliva sample is obtained with a saliva collection device without virus-specific enrichment.

4. The method of claim 1 further comprising isolating at least one of viral influenza A RNA and viral influenza B RNA from the sample.

5. The method of claim 4 wherein the detecting comprises amplifying the RNA by RT-PCR and detecting the amplified RNA.

6. The method of claim 1 wherein the detecting comprises examining the saliva sample immunologically for the presence of at least one of the influenza A virus and the influenza B virus.

7. The method of claim 6 further comprising treating the sample with a lysing buffer to release a viral nucleoprotein of at least one of the influenza A virus and influenza B virus.

8. The method of claim 7 wherein the nucleoprotein is detected immunologically.

9. A method for detecting in a subject an infection with influenza A virus and/or influenza B virus comprising:
   (a) obtaining a saliva sample from the subject;
   (b) treating the sample with a lysing agent to release viral nucleoprotein of at least one of influenza A virus and influenza B virus;
   (c) contacting the treated sample with at least one antibody to the at least one viral nucleoprotein; and
   (d) detecting whether the at least one antibody binds to the at least one viral nucleoprotein, thereby detecting an infection with at least one of influenza A virus and influenza B virus.

10. The method of claim 9, wherein the saliva sample is obtained from spontaneously formed saliva.

11. The method of claim 9, wherein the saliva sample is obtained with a saliva collection device without virus-specific enrichment.

12. A method for detecting an infection with influenza A virus and/or influenza B virus comprising:
   (a) obtaining a saliva sample;
   (b) amplifying viral RNA in the sample by RT-PCR;
   (c) contacting the amplified RNA with at least one hybridization probe for the viral RNA of at least one of influenza A virus and influenza B virus; and
   (d) detecting whether the at least one probe hybridizes to the amplified RNA, thereby detecting an infection with at least one of influenza A virus and influenza B virus.

13. The method of claim 12, wherein the saliva sample is obtained from spontaneously formed saliva.

14. The method of claim 12, wherein the saliva sample is obtained with a saliva collection device without virus-specific enrichment.

15. A test kit for the detection of an infection with influenza A virus and/or influenza B virus comprising:
   (a) a device for collecting a saliva sample, and
   (b) reagents for detecting at least one of influenza A virus and influenza B virus in the saliva sample.

16. The kit of claim 15 wherein the reagents are suitable for detecting the nucleic acid of at least one of influenza A virus and influenza B virus.

17. The kit of claim 15 wherein the reagents are suitable for immunologically detecting the nucleoprotein of at least one of influenza A virus and influenza B virus.

18. The kit of claim 15 wherein the device for collecting a saliva sample is suitable for collecting spontaneously formed saliva.

* * * * *